US005693040A

United States Patent [19]

Prior

[11] Patent Number: 5,693,040

[45] Date of Patent: Dec. 2, 1997

[54] TWO COMPARTMENT INFUSION BAG

[75] Inventor: Francis George Prior, Longniddry, United Kingdom

[73] Assignee: East & Midlothian NHS Trust, Pinkieburn, Scotland

[21] Appl. No.: 454,342

[22] PCT Filed: Dec. 15, 1993

[86] PCT No.: PCT/GB93/02553

§ 371 Date: Aug. 15, 1995

§ 102(e) Date: Aug. 15, 1995

[87] PCT Pub. No.: WO94/13246

PCT Pub. Date: Jul. 23, 1994

[51] Int. Cl.[6] .......... A61B 19/00

[52] U.S. Cl. .......... 604/410; 604/246

[58] Field of Search .......... 604/408, 409, 604/410, 246

[56] References Cited

U.S. PATENT DOCUMENTS

| | | | |
|---|---|---|---|
| 2,542,461 | 2/1951 | Bay | 128/227 |
| 2,640,358 | 6/1953 | McClure et al. | 73/421.5 |
| 2,648,333 | 8/1953 | Cutter | 128/214 |
| 2,786,467 | 3/1957 | Price | 128/214 |
| 2,848,995 | 8/1958 | Ryan | 128/214 |
| 3,028,863 | 4/1962 | Mattson | 604/410 |
| 3,030,952 | 4/1962 | Elder | 128/214 |
| 3,949,745 | 4/1976 | Howell | 128/214 C |
| 4,000,738 | 1/1977 | Howell | 128/214 D |
| 4,432,763 | 2/1984 | Manschot et al. | 604/262 |
| 4,484,920 | 11/1984 | Kaufman et al. | 604/410 |
| 4,507,114 | 3/1985 | Bohman et al. | 604/410 |
| 4,576,603 | 3/1986 | Moss | 604/410 |
| 5,114,004 | 3/1992 | Isono et al. | 604/410 |

FOREIGN PATENT DOCUMENTS 1494411 of 0000 United Kingdom .

*Primary Examiner*—John G. Weiss
*Assistant Examiner*—Ki Yong O
*Attorney, Agent, or Firm*—Young & Basile, P.C.

[57] ABSTRACT

The present invention provides a bag container (1) suitable for use in dispensing liquid e.g. for intravenous administration, at a controlled rate. The bag comprises a first compartment (2) for holding a main body of liquid to be dispensed, and a second compartment (4) for holding a small portion of the liquid (6) and disposed substantially below the first compartment (2). The first compartment (2) is connected to the second compartment (4) by a syphon conduit (8), and the second compartment (4) is provided with an outlet (18). The second compartment (4) is formed and arranged so that syphoning can be maintained in use of the bag (1) in a dispensing attitude thereof, whereby a substantially constant head of liquid (6) is maintained in the second compartment (4) during dispensing of most of said liquid (6) held in said bag container (1).

14 Claims, 2 Drawing Sheets

TWO COMPARTMENT INFUSION BAG

Figure 1:
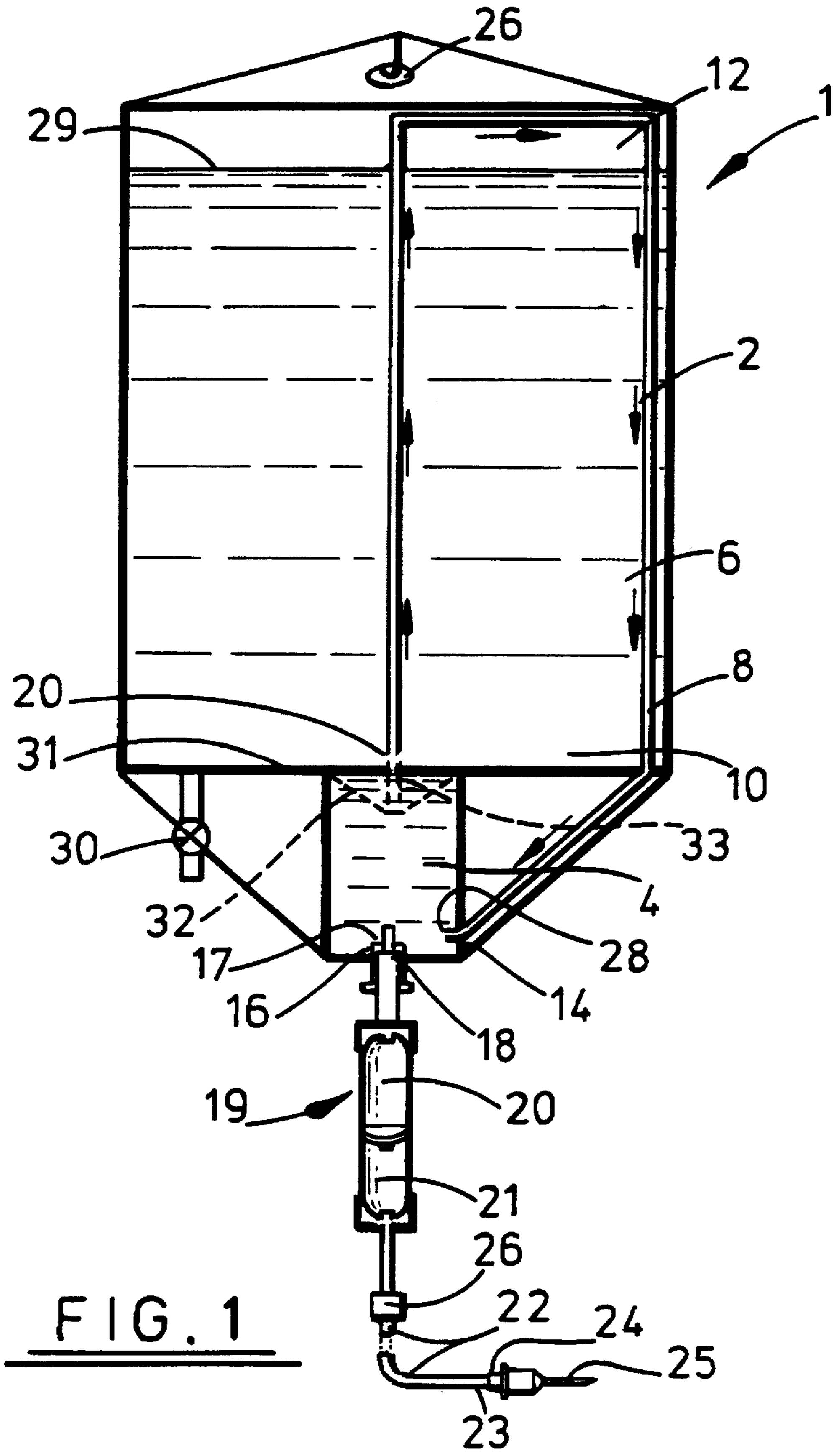

The present invention relates to a bag for use in containing a liquid and from which the liquid may be dispensed. The bag is particularly directed to medical applications such as for containing a solution for intravenous or otherwise administration to a patient but not exclusively.

Conventionally a solution or blood product to be intravenously administered or otherwise dispensed is contained in a flexible flat expandable container for containing blood, blood products and the like of the type available from for example Baxter-Travenol, which is connected to a patient by a tube and a giving set using a gravity feed to dispense the solution. One of the major practical problems encountered with this type of system is that the rate of flow of solution from the bag diminishes as the amount of fluid remaining in the bag reduces and the pressure head of the solution in the bag reduces. Accordingly it is necessary for the rate of dispensing to be adjusted every now and again via the giving set to compensate for the reduction in pressure, due to the change in head of liquid.

There are commercially available electro-mechanical apparatus which dispense solutions at a more or less constant rate by pumping it at a controlled rate. Such apparatus is however cumbersome, expensive and require a power source to operate.

It is an object of the present invention to avoid or minimise one or more of the foregoing disadvantages.

The present invention provides a bag container suitable for use in dispensing liquid at a controlled rate, which bag is supportable, in use, in a dispensing attitude and which comprises a first compartment means formed and arranged for holding a main body of liquid to be dispensed, and a second compartment means formed and arranged for holding a small portion of said liquid and disposed substantially below said first compartment means in said dispensing attitude of the bag, said first compartment means being connected to an inlet of said second compartment means by a syphon conduit means, and said second compartment means being provided with outlet means for said liquid, said second compartment means with its inlet and outlet means being formed and arranged so that syphoning can be maintained in use of the bag in said dispensing attitude thereof, whereby in use, a substantially constant head of liquid is maintained in said second compartment means during dispensing of most of said liquid held in said bag container.

Thus with a bag container according to the present invention, substantially all the solution contained in the bag may be dispensed at a more or less constant rate of delivery without the need for adjustment. In this connection it will be understood that once the first compartment has been drained and/or the siphon broken, then the head in the second compartment will begin to reduce and there will then be a reduction in flow rate (see also Example hereinbelow). Accordingly it is desirable that the capacity of the second compartment should be quite small relative to that of the first compartment in order to maximise the amount of fluid held in the bag which is delivered at a substantially constant rate. In general the ratio of size between the first compartment and second compartment may be in the region of from 60:1 to 20:1, preferably from 40:1 to 30:1. Preferably said first compartment has a volume of 0.5 to 6, e.g. 0.5 to 3, liters desirably from 1 to 3, e.g. 1 to 2.5, liters. It will be appreciated though that other ratios and sizes may be used for particular applications.

The syphon conduit means may be connected and extend between said first and second compartment means in any convenient manner provided the inlet to the syphon conduit is above the outlet thereof (at the inlet to the second compartment) with said bag container in said dispensing attitude. Most preferably though said syphon conduit means extends upwardly from said inlet thereof, proximal the base of said first compartment means, (in the dispensing attitude of the bag) to a greater or lesser extent, but advantageously up towards the upper end of said first compartment means, most desirably to a level above the maximum level of fluid in the bag in order to negate the effects of hydrostatic pressure, and then downwardly to an outlet of said syphon conduit proximal a base portion of said second compartment means, so that more or less all the liquid contained in said first compartment means may be transferred to said second compartment means, with said bag container being in said dispensing attitude.

Preferably said syphon conduit means is secured to a side wall of the bag container, most conveniently by being formed integrally therewith. Advantageously said syphon conduit means is in the form of an elongate hollow tube which may be formed and arranged inside said bag container or alternatively could extend to a greater or lesser extent outside said bag container.

It will be of course be appreciated that, provided a suitable difference in head is maintained between the inlet and outlet of the siphon tube, the precise form and position of the second compartment is not critical.

Thus for example an upper portion of the second compartment may "overlap" with or extend alongside a lower part of the first compartment.

Although it would in principle be possible to fill the bag via the outlet from the second compartment and the syphon tube, desirably said first compartment means is provided with a separate inlet means to facilitate filling of said first and second compartment means with a liquid to be dispensed.

Preferably said bag container is provided with connector means or the like above said first compartment means for attaching said bag container to a suitable support means for supporting said bag in said dispensing attitude.

In use of the bag it is of course necessary that a syphon should be established with a substantially full syphon tube. Priming of the syphon to fill the syphon tube may be effected by at least partly filling the first compartment via the second compartment and syphon tube. Complete filling by this route would normally be less preferred due to the relatively small capacity of the syphon tubes normally used. A particular advantage of the present invention is however that, where a substantially flexible and resiliently collapsible wall second compartment is used, then priming may be simply effected by squeezing together the second compartment walls so as to expel air from the second compartment through the syphon tube into the first compartment, and liquid then being drawn back into the expanding second compartment through the syphon tube thereby filling the latter.

The outlet means of said second compartment means is conveniently provided with a giving set or administration set of generally known type and description which normally comprises at least a valve means formed and arranged to regulate and control the rate at which liquid is dispensed from the bag container and usually includes an enlarged diameter portion forming a drip chamber whereby the delivery rate may conveniently be monitored in drips per minute (DPM). It is a particular advantage of the present invention though that very simple forms of giving set comprising as little as a screw clamp can be used without the need for frequent adjustment during dispensing to provide the required generally constant flow rate.

It will be understood that the diameter of the syphon conduit means will restrict the rate at which the liquid may be dispensed from the bag and that the syphon conduit means must be capable of delivering liquid from the first compartment means to the second compartment means at a rate at least equal to the maximum rate at which liquid is required to be dispensed at from the second compartment means outlet means. Desirably there is used a syphon conduit means having an internal diameter of from 0.5 to 5 mm e.g. about 1 mm.

Figure 2:
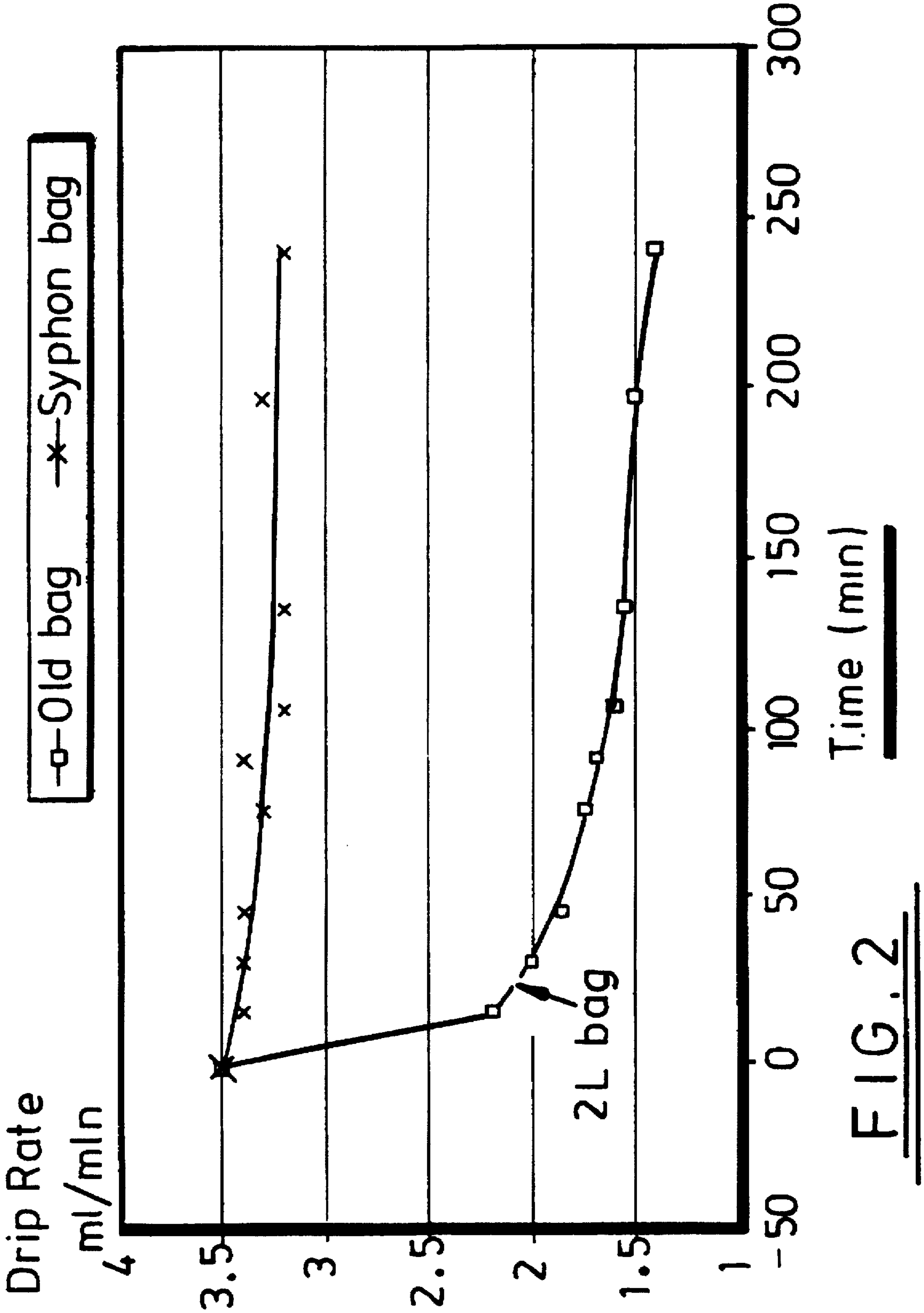

Further preferred features and advantages of the present invention will appear from the following detailed description given by way of example of a preferred embodiment illustrated with reference to the accompanying drawing in which:

FIG. 1 is a side view of a bag container according to the invention, with a giving set connected thereto; and FIG. 2 is a graph comparing the delivery rates (without intervention or adjustment) for a bag according to FIG. 1 and a conventional single compartment bag.

In more detail the bag container, generally indicated by reference number 1, comprises a larger upper compartment 2 and a lower, smaller compartment 4 for holding a liquid 6 to be dispensed. An elongate syphon tube 8 extends from the bottom 10 up to the top 12 of the upper compartment 2 and then bends around and returns down into the bottom 14 of the lower compartment 4. Liquid 6 contained in the upper compartment 2 is syphoned into the lower compartment 4 via the syphon tube 8, due to the differential liquid head between the two compartments 2, 4.

At the base 15 of the second compartment 4 is provided a connector 16 with a membrane seal 17 for receiving the closure piercing device 18 of a conventional giving or administration set 19 which also optionally includes a filter 20 (for use in removing fibrin clots where the bag contains blood) and a drip chamber 21. Downstream of the drip chamber 21 is provided a flexible delivery tube 22 e.g. of silicone rubber which has at its distal end 23 a male liner connector 24 for connection to a hyprodermic needle 25. An adjustable clamp 26 is provided on the tube 22 for regulating the rate of flow through the giving set 19. It will of course be understood that the giving set 19 itself should be "primed" prior to use to flush air out of the system in well known manner e.g. by repeatedly squeezing and releasing the flexible walls of the filter chamber 20.

In use, once the clamp 26 has been opened on the delivery tube 22 of the giving set 19, liquid will be dispensed at a regular controlled rate. It will be seen that a substantially constant head of liquid 6 (i.e. that between the inlet 20 to the elongate syphon tube 8 at the bottom 10 of the upper compartment 2 and the outlet 28 of the elongate syphon tube 8 at the bottom 14 of the lower compartment 4) is achieved irrespective of the level 29 of liquid 6 in the upper compartment 2.

The bag container 1 is also provided with an inlet valve 30 in the bottom 10 of the upper compartment 2 so that the compartment 2 may be filled with liquid 6 to be dispensed. The bag container 1 is further provided with a support loop 26 for supporting the bag 1 and its contents on a suitable support (not shown) in the dispensing attitude of the container bag.

The bag container may be made from any suitable flexible, transparent material which may be readily sterilized. Preferably there is used a polymeric material such as silicone rubber, polyalkane e.g. polyethylene or polypropylene, polyvinyl chloride etc.

FIG. 2 shows a graph of the change in drip rate of a phsyiological saline solution with time over a period of 4 hours. For comparison the abovedescribed bag container of the present invention (2 liters capacity with 50 ml lower compartment) is compared with a conventional bag (2 liters capacity). The initial drip rate is 60 D.P.M. for both bags corresponding to a delivery rate of about 3.5 ml/min. As will be seen from the graph the drip rate from the bag container of the present invention stays more or less constant over time, whereas the conventional bag shows a significant drop in drip rate over time.

Various modifications may be made without departing from the scope of the present invention. Thus for example, the elongate syphon tube may be formed integrally within the wall of the bag container. Also the base 31 of the upper compartment 2 could be provided with a recess 32 into which the inlet 20 of the syphon tube 8 is extended 33 to maximise the amount of liquid 6 syphoned off from the upper compartment 2.

I claim:

1. A bag container suitable for use in dispensing liquid at a controlled rate, which bag is supportable, in use, in a dispensing attitude and which bag comprises a first compartment means for holding a first quantity of liquid to be dispensed, and a second compartment means for holding a second quantity of said liquid smaller than said first quantity, said second compartment means disposed substantially below said first compartment means in said dispensing attitude of the bag, said first compartment means being connected to an inlet of said second compartment means by a syphon conduit means, and said second compartment means being provided with outlet means for said liquid, said second compartment means with its inlet and outlet means being formed and arranged so that syphoning can be maintained in use of the bag in said dispensing attitude thereof, whereby in use, flow rate variation of liquid dispensed from said second compartment means during dispensing of most of said liquid held in said bag container is restricted.

2. A bag container according to claim 1 wherein said second compartment means has a volume capacity of not more than one twentieth of that of the first compartment means.

3. A bag container according to claim 1 wherein the first compartment means has a first volume capacity and the second compartment means has a second volume capacity, said first volume capacity being from 20 to 60 times the second volume capacity.

4. A bag container according to claim 1 wherein said first compartment means has a volume capacity of from 0.5 to 3 liters.

5. A bag container according no claim 1 wherein said second compartment comprises a flexible bag.

6. A bag container according to claim 1 wherein said syphon conduit means extends from an inlet thereof, closely proximal a base of said first compartment means towards an upper end of said first compartment means, and then to an outlet of said syphon conduit closely proximal a base portion of said second compartment means, so that substantially all the liquid contained in said first compartment means may be transferred to said second compartment means, with said bag container being in said dispensing attitude.

7. A bag container according to claim 1, wherein said syphon conduit means is connected to a side wall of the bag container.

8. A bag container according to claim 9 wherein the outlet of said second compartment is connected to a giving set.

9. A bag container according to claim 1 which bag is substantially filled with a physiologically acceptable fluid suitable for intravenous administration.

10. A bag container according to claim 3 wherein said first volume capacity is from 30 to 40 times the second volume capacity.

11. A bag container suitable for use in dispensing liquid at a controlled rate, which bag is supportable, in use, in a dispensing attitude and which bag comprises a first compartment means for holding a first quantity of liquid to be dispensed, and a second compartment means for holding a second quantity of said liquid smaller than said first quantity, said second compartment means being disposed substantially below said first compartment means in said dispensing attitude of the bag, said first compartment means being connected to an inlet of said second compartment means by a siphon conduit means, and said second compartment means being provided with outlet means for said liquid, said second compartment means with its inlet and its outlet means being disposed so that syphoning can be maintained in use of the bag in said dispensing attitude thereof, said outlet portion of said siphon conduit means being in a fluid-tight connection with said inlet of said second compartment means, and the outlet means of the second compartment means being in fluid-tight connection with a giving set, so that, in use of the bag, the interior of the second compartment means is isolated from the interior of the first compartment means by liquid in the siphon conduit means whereby the outlet end of the siphon conduit means is subjected to a pressure which is controlled by the back-pressure present inside the second compartment means when the outlet means thereof is connected in use of the bag to a said giving set, and flow rate variation of liquid dispensed from said second compartment means during dispensing of most of said liquid held in said bag container is substantially restricted.

12. A bag container according to claim 11 wherein the giving set comprises at least one valve means for regulating and controlling the rate at which liquid is dispensed from the bag container.

13. A bag container according to claim 12 wherein said giving set includes an enlarged diameter portion forming a drip chamber whereby a liquid delivery rate may be monitored in drips per minute.

14. A container suitable for use in dispensing liquid at a controlled rate, which bag is supportable, in use, in a dispensing attitude, said bag container comprising:

first compartment means for holding a first quantity of liquid to be dispensed;

second compartment means for holding a second quantity of said liquid smaller than said first quantity, said second compartment means disposed substantially below said first compartment means in said dispensing attitude of the bag and having outlet means for said liquid; and siphon conduit means comprising a first end in fluid flow communication with said first compartment means closely proximal a lower end thereof and a second end in fluid flow communication with said second compartment means closely proximal a lower end thereof, said syphon conduit means extending from said first end toward an upper end of said first compartment means, and further extending to said second end, whereby syphoning may be maintained in said dispensing attitude to cause said fluid in said first compartment means to flow into said second compartment means.

* * * * *

UNITED STATES PATENT AND TRADEMARK OFFICE
CERTIFICATE OF CORRECTION

PATENT NO. : 5,693,040

DATED : December 2, 1997

INVENTOR(S) : Francis George Prior

It is certified that error appears in the above-identified patent and that said Letters Patent is hereby corrected as shown below:

Column 6, Line 9, delete "container" and insert --bag container--.

Signed and Sealed this

Twenty-third Day of March, 1999

Attest:

Q. TODD DICKINSON

*Attesting Officer* *Acting Commissioner of Patents and Trademarks*